Figure 1:
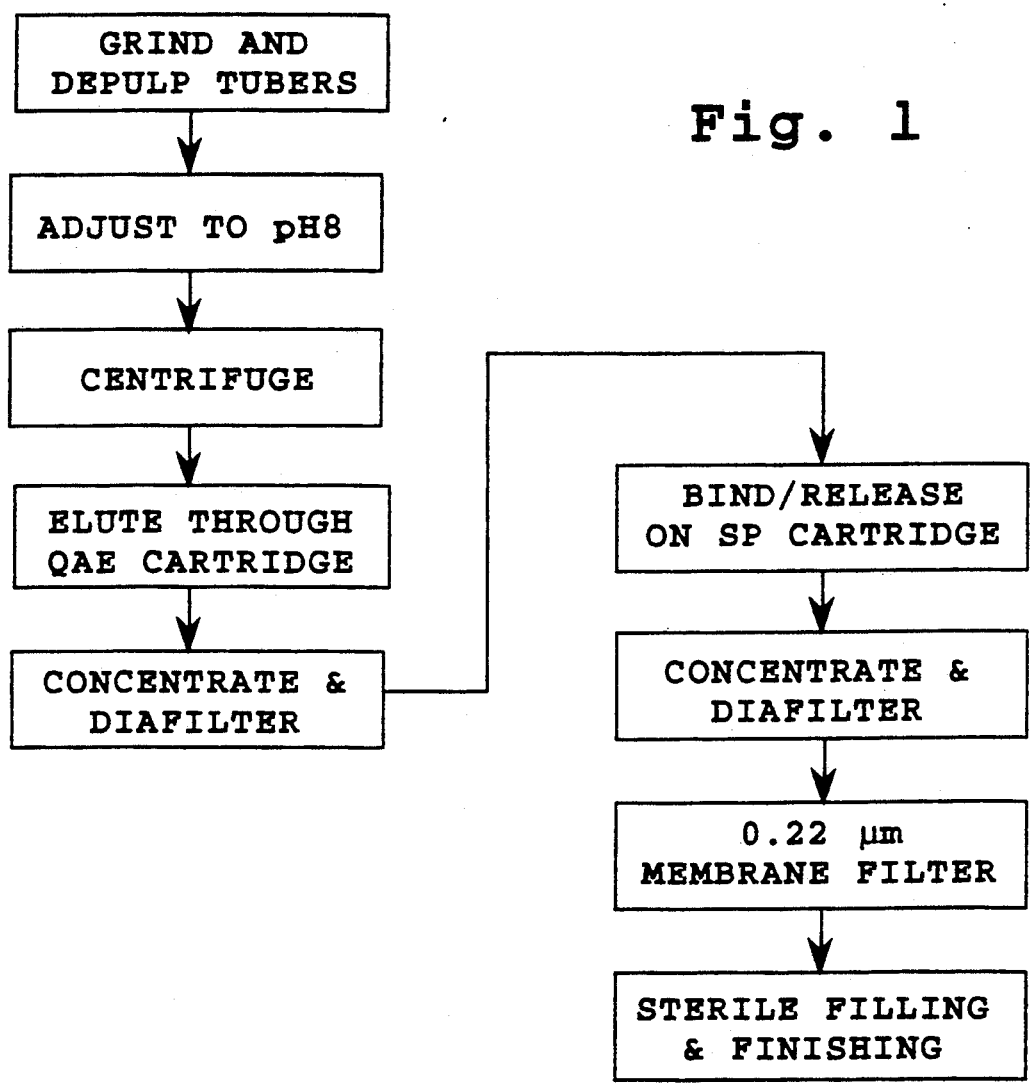

United States Patent [19]

Wu et al.

[11] Patent Number: 5,077,390

[45] Date of Patent: Dec. 31, 1991

[54] PURIFIED TRICHOSANTHIN AND METHOD OF PREPARATION

[75] Inventors: Paul S. Wu, San Francisco; Susan B. Wade, Fremont; Raul R. Soikes, Sunnyvale, all of Calif.

[73] Assignee: Genelabs, Incorporated, Redwood City, Calif.

[21] Appl. No.: 404,328

[22] Filed: Sep. 7, 1989

Related U.S. Application Data

[62] Division of Ser. No. 333,181, Apr. 4, 1989.

[51] Int. Cl.$^5$ .......................... C07K 3/22; C07K 3/26; C07K 3/28; C07K 15/10

[52] U.S. Cl. .................................... 530/370; 530/416; 530/417; 530/412

[58] Field of Search ............... 530/416, 417, 350, 370, 530/412

[56] References Cited

U.S. PATENT DOCUMENTS 4,705,686 11/1987 Scott et al. ............................ 424/92
4,795,739 1/1989 Lifson et al. ............................ 514/8

FOREIGN PATENT DOCUMENTS 0286441 12/1988 European Pat. Off. .

OTHER PUBLICATIONS

Maraganore et al., 1987, J. Biol. Chem. 262(24):11628-11633.
Sofer, G., 1984, Bio/Technology, Dec., pp. 1035-1038.
Yeung, et al., 1986, Int. J. Peptide Protein Res. 27:325-333.
Yeung et al., 1987, Immunopharmacology and Immunotoxicology 9(1):25-46.
"ZetaPrep® Ion Exchange Chromatography", Life Sciences Division, of Cuno, Inc.

*Primary Examiner*—Margaret Moskowitz
*Assistant Examiner*—Keith C. Furman
*Attorney, Agent, or Firm*—Peter J. Dehlinger; Gary R. Fabian

[57] ABSTRACT

A substantially pure, hemagglutinin-free composition of trichosanthin, and a method of producing the composition is disclosed. A plant extract from *Trichosanthes kirilowii* is contacted with an anionic exchange resin to remove contaminating hemagglutinins, and trichosanthin is further purified from the extract by cation exchange chromatography to a purity of greater than 95%.

5 Claims, 3 Drawing Sheets

PURIFIED TRICHOSANTHIN AND METHOD OF PREPARATION

This is a divisional application of copending application Ser. No. 07/333,181, filed Apr. 4, 1989.

FIELD OF THE INVENTION

The present invention relates to a purified trichosanthin (TCS) composition and to a novel method of producing the composition.

REFERENCES

Armstrong, W. H., Presented at the International Conference on AIDS, 23-25 June, 1986, Paris.

Calderwood, S. B., et al., Proc Nat Acad Sci USA, 84:4364 (1987).

Chayt, K. J., et al., JAMA, 256:2356 (1986).

Coleman, W. H., et al., Biochem Biophys Acta, 696:239 (1982).

Gartner, S., Science, 233:215 (1986a).

Gartner, S., et al., JAMA, 256, 2365 (1986b).

Gasperi-Campani, et al., FEBS Lett, 76(2):173 (1977).

Grasso, S., et al., Agric Biol Chem, 52(4):1095 (1988).

Gu, Zi-wei, et al., Acta Chemica Sinica, 43:943 (1984).

Ho, D. D., et al., J Clin Invest, 77:1712 (1986).

Hsu, K. J., et al., Acta Zool Sin, 22:149 (1976).

Hwang, Y. N., Chinese J Integrated Trade and Western Medicine, 7:154 (1987).

Irvin, J., Arch Biochem Biophys, 169:5221 (1985).

Kao, H., et al., Acta Biol Exp Sin, 11:253 (1978).

Kezhan, Pan, et al., Supplement of Proc of China-Japan Bilateral Symposium on Biophys, Wuxi, China (May 1985).

Koenig, S., et al., Science, 233:1089 (1986).

Kuo-Fen, C., et al., Obs and Gyn, 59(4):494 (1982).

Law, L. K., et al., J Reprod Fert, 69:597 (1983).

Lifson, J. D., et al., Science, 232:1123 (1986a).

Lowry, O. H., et al., J Biol Chem, 193:265 (1951).

Maraganove, J. M., et al., J Biol Chem, 262(24):11628 (1987).

Olnes, S., Nature, 328:474 (1987).

Olnes, S., et al., in Molecular Action of Toxins and Viruses, (Elsevier, 1982), Chapter 3.

Steicher, H. Z., et al., JAMA, 256:2390 (1986).

U.S. Pharmacopia, XXI, p. 1105 (1985).

Wang, Yu, et al., Int. Symposium on Org Chem of Medicinal Natural Products, Shanghai China (November 1985).

Xiong, Y. Z., et al., Acta Zool Sin, 11:236 (1976).

Xuejan, Z., et al., Nature, 321:477 (1986).

Yeung, H. W. et al., Int J Peptide Protein Res., 27:325 (1986).

BACKGROUND OF THE INVENTION

TCS is a plant protein which is obtained from the *Trichosanthes kirilowii* root tuber. The protein, which is also known as alpha-TCS (Law) and Radix trichosanthis (Kuo-Fen), is a basic, single-chain protein which has been reported to containing about 224 (Gu) to 234 (Xuejan) amino acid residues, and reported to have a molecular weight of about 24,000 daltons. The protein sequence of TCS has been completed (Gu; Wang), and a molecular model has been derived from cytofluorographic X-ray analysis (Kezhan).

It has been shown that TCS is a potent inhibitor of protein synthesis in a cell-free lysate system (Maraganove). This activity is consistent with the observed homology in amino acid sequence between TCS and the A chain of ricin, a ribosome-inactivating protein (RIP) which shows amino acid homology with a number of other RIPs, including abrin A chain (Olnes, 1982, 1987) and modeccin (Olnes, 1982), and various single-chain ribosome-inactivating proteins, such as pokeweed antiviral protein (PAP) (Irvin), RIPs from a variety of other plants (Coleman; Grasso; Gasperi-Campani) and the A subunit of Shiga-like toxins from *E. coli* (Calderwood).

TCS, or plant extracts containing TCS, have been used in China as an abortifacient agent for inducing abortion in humans, particularly during midtrimester (14 to 26 weeks). As such, the drug has been administered by intramuscular, intravenous, or intraamniotic routes. The phenomenon of mid-term abortion has been attributed to the selective destruction of placental villi. Other studies indicate that the syncytiotrophoblast is preferentially affected (Hsu; Kao) and that secretion of hCG may be impaired (Xiong). TCS has also been shown to have a suppressive effect on human choriocarcinoma, and the protein appears to be able to pass the blood/brain barrier (Hwang).

Co-owned U.S. Pat. No. 4,795,739 for "Method of Inhibiting HIV" describes the use of TCS for inhibiting HIV (Human Immunodeficiency Virus) proliferation in infected human T cells and macrophages, for treating HIV infection in humans. In view of the significant therapeutic use of TCS, it would be valuable to obtain the protein in substantially pure form by preparation methods which are suited to large-scale processing.

Methods of preparing TCS have been reported (Yeung). These methods typically involve an initial aqueous extraction of fresh root tubers of *T. kirilowii*, and lyophilization of the extract supernatant. The resulting powder is dissolved in water medium, followed by addition of solvent, such as an aqueous acetone mixture, to yield a precipitate containing TCS. After removal of the precipitate by centrifugation, additional solvent is added to the supernatant, yielding a second TCS-containing precipitate fraction on centrifugation. Both precipitates are re-extracted with aqueous medium, giving soluble protein fractions containing partially purified TCS.

The soluble fraction from the second-solvent precipitate can be further purified by cation exchange column chromatography, using a NaCl gradient to release the protein. The eluate profile from the column indicates the presence of contaminating proteins on both sides of the protein peak identified as TCS.

Alternatively, the soluble fraction from the first-or from the second-solvent precipitate can be purified by an initial pass through an anion exchange resin column, and the eluate further purified by cation exchange column chromatography. Although the resulting protein is somewhat more pure than that from the method involving cation exchange chromatography alone, the cation exchange elution profile still shows the presence of prominent side peaks, as evidenced by size-exclusion HPLC.

Studies carried out in support of the present application, and discussed below, indicate that the TCS protein isolated by the above methods contains readily detectable contaminating proteins. Based on the observed hemagglutination activity of the purified protein preparation, at least one of the contaminants is a hemagglutinin. The above-described purification methods are also difficult to adapt to large scale, in view of the need for volatile organic solvent extraction.

SUMMARY OF THE INVENTION

One object of the present invention is to provide a substantially pure TCS composition, and in particular, a composition which is substantially free of hemagglutinins.

Another object of the invention is to provide a method for producing purified TCS which is easily adapted to large-scale processing.

In practicing the TCS purification method of the invention, a clarified plant extract from the roots of *T. kirilowii* is contacted with an anion exchange material for removal of extract contaminants which bind to the material. According to one aspect of the purification method, it has been found that carrying out the anion exchange material binding step in a low-conductivity buffer is effective to remove substantially all hemagglutinins from the extract. The extract is also contacted with a cation exchange material, under conditions which separate TCS from extract contaminants which bind more weakly to the cation exchange material than TCS at a low buffer conductivity, and from contaminants which bind more strongly to the cation exchange material than TCS at a higher conductivity.

In a preferred embodiment, clarified extract is first contacted with the anion exchange material, and the eluate from the anion exchange material is treated by diafiltration to remove UV-absorbing contaminants having molecular weights of less than about 10,000 daltons. The diafiltration step also serves to bring the eluate to a pH and conductivity suitable for the subsequent exchange step. The eluate is now contacted with the cation exchange material, which is washed extensively to remove loosely bound contaminants. The TCS protein is released from the cation exchange material, in substantially pure form, by washing the column with a selected, higher conductivity buffer.

The purity of the TCS protein, as judged by HPLC chromatography and SDS gel electrophoresis, is greater than about 95% pure, and preferably greater than 98% pure. The protein composition shows little or no hemagglutination activity.

In another aspect, the invention includes a TCS composition produced by the above purification method, a substantially pure TCS composition (having a purity of greater than about 95%), and a TCS composition which is substantially free of hemagglutinins.

These and other objects and features of the invention will become more fully apparent when the following detailed description of the invention is read in conjunction with the accompanying drawings.

BRIEF DESCRIPTION OF THE DRAWINGS

FIG. 1 is a flow diagram of steps in the TCS-purification method of the invention;

FIGS. 2A-2D show size-exclusion HPLC profiles of (2A protein extract from *T. kirilowii*; (2B) extract material after removal of hemagglutinins and other contaminants which bind to an anion-exchange material under low-conductivity conditions; (2C), partially purified extract after concentration and diafiltration a using low-molecular weight cut-off membrane; and (2D), after final TCS purification by cation-exchange material chromatography;

FIG. 3 shows SDS polyacrylamide gel electrophoresis of purified trichosanthin prepared according to invention and stained with Coomassie blue, at loaded protein amounts ranging from 0.25 μg to 40 μg/gel; and FIG. 4 shows SDS polyacrylamide gel electrophoresis of the trichosanthin preparation applied in the FIG. 3 gels, and stained with silver, at loaded protein amounts ranging from 0.005 μg to 10 μg.

DETAILED DESCRIPTION OF THE INVENTION

Method of Purifying TCS

FIG. 1 outlines the general method for producing purified TCS according to the method of the invention. A clarified extract of roots of *T. kirolowii* is obtained, conventionally, using peeled and sliced root tubers obtained from fresh or frozen tubers. The tubers are conveniently processed in a juicer or blender, and filtered to remove pulp. The pH is adjusted to 8.0 and the material is allowed to stand overnight, then clarified by centrifugation, following the general method of Example 1. The volume of aqueous medium used for processing is not critical, but is preferably just large enough to facilitate homogenization. The medium will usually be a salt solution, such as normal saline (0.9% w/v NaCl), phosphate buffer or phosphate buffered saline at a preferred pH of between about 7-9.

A typical size-exclusion high pressure liquid chromatography (HPLC) profile (using BIOSIL TSK125 column) of the clarified extraction mixture is shown in FIG. 2A. The 11.3 min. retention time (RT) peak in this profile corresponds to TCS.

In the following discussion, the peak retention time values referred to were obtained by size-exclusion HPLC, using either BIOSIL TSK250 or BIOSIL TSK125. In particular, BIOSIL TSK250 was used to obtain better resolution of high-molecular weight species. Those retention-time values which were obtained using TSK125 and specifically designated in parenthesis and correspond to peaks shown in FIGS. 2A-2D. All other retention-time values were obtained by TSK250 HPLC. These retention time values are not absolute values, but will vary from system to system according to flow rate, column length, temperature and system configuration.

Following clarification, the extract is diluted with water to the desired conductivity and contacted with an anion exchange material. This is preferably done by passing the diluted clarified extract through a column packed with the anion exchange material. The anion exchange material preferably has a quaternary ethylamino ethyl (QAE) functional group, as exemplified by QAE ZETAPREP™ which is supplied commercially in cartridge form. Other known anion exchangers, such as diethylamino ethyl (DEAE) type anion exchange materials may also be employed.

According to one aspect of the method of the invention, it has been discovered that the degree of purification, and particularly the degree of removal of hemagglutinins from the extract, can be enhanced substantially by carrying out the anion exchange binding under low conductivity conditions. Studies presented in Example 2 compare the effectiveness of the anion exchange binding to QAE ZETAPREP™ at 20 mM, 40 mM, and 50 mM phosphate buffer, pH 8. The conductivity of the 20 mM buffer is about 3.1 mS/cm, and that of 50 mM buffer, about 6.5 mS/cm.

As discussed in the example, the effectiveness of the low conductivity medium is due in part to precipitation of a protein contaminant having an HPLC peak of about 6.8 min RT. This contaminant does not bind to the anion exchange material, but in precipitated form, is filterable before applying the solution to the anion exchange material. HPLC analysis using BIOSIL TSK250 shows that the 6.8 min RT peak present in the extract is substantially removed after the anion exchange step carried out at low ionic strength.

Figure 2:
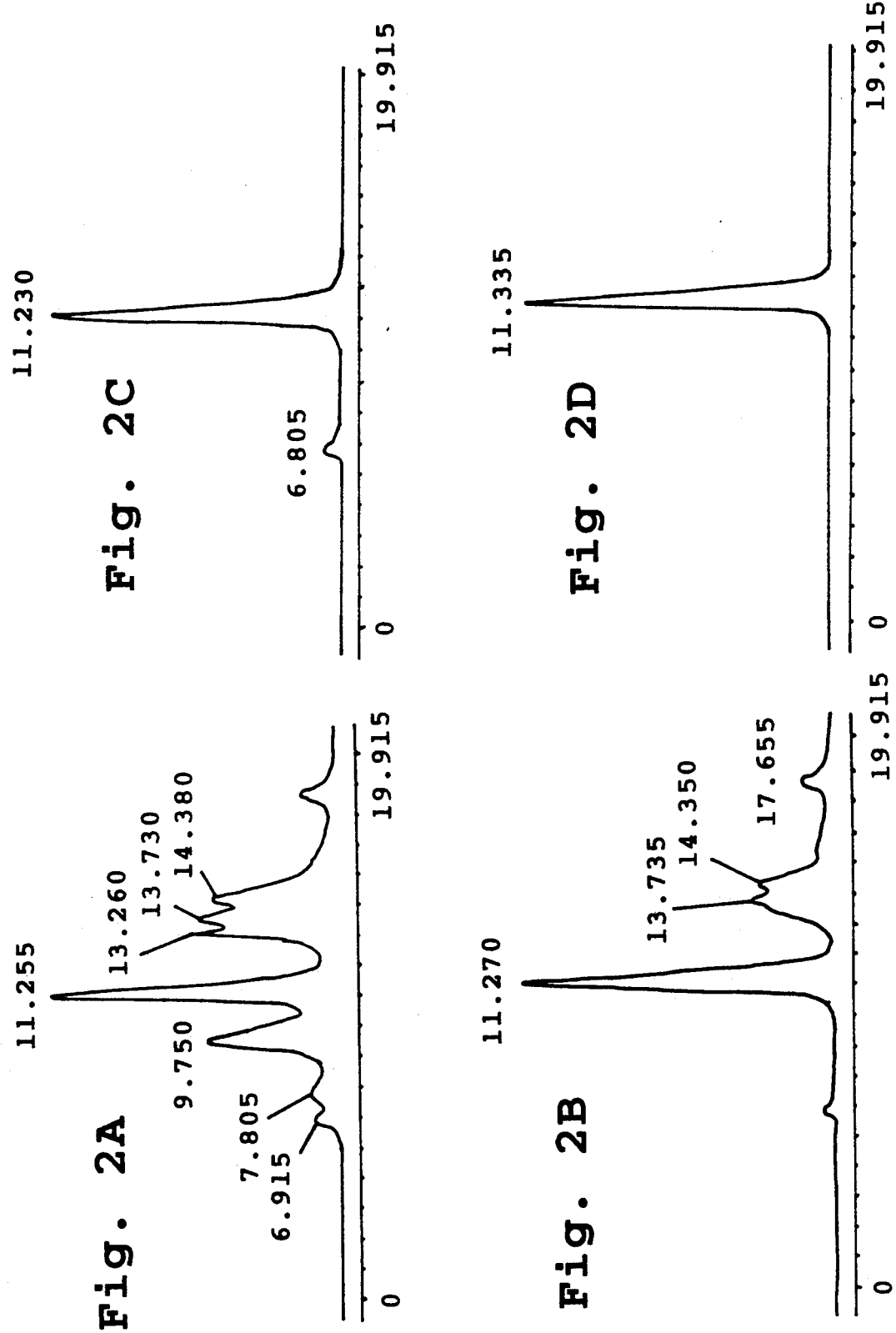

The low ionic strength also produces enhanced removal of contaminants associated with 9 min and 10.3 min RT peaks (obtained from BIOSIL TSK250 and seen as a combined 9.75 min RT peak on BIOSIL TSK125 in FIG. 2A) As noted in Example 2, greater contamination of the flowthrough with the 9 min RT peak occurs at high protein loading and/or at buffer conductivities greater than about 5.5 mS/cm. The amount of 10.3 min RT peak in the flowthrough decreased steadily with decreased buffer concentration, and at 3 mS/cm buffer no 10.3 min RT peak was observed in the flowthrough.

According to another important feature of the anion exchange step, the low ionic strength eluate containing the desired TCS is substantially free of hemagglutinins. This is seen in Example 3, which describes a hemagglutination study carried out with total extract and three fractions from the initial eluate wash from the anion exchange column, at 100 mM (about 11.92 mS/cm conductivity) and 20 mM buffer concentrations (about 3.1 mS/cm). In each case, three eluate fractions were assayed for hemagglutination activity. As seen from Table III in the example, the later eluate fractions (F5 and F9) at 100 mM buffer contained readily detectable levels of hemagglutinins. By contrast, using 20 mM buffer, none of the eluate fractions showed any detectable hemagglutination. The "P. A." fraction shown in the figure is a TCS preparation purified according to prior art methods (Yueng). As seen, the fraction contains readily detectable hemagglutinin contaminants.

To obtain the low conductivity required of the anion-exchange buffer, the clarified extract may be diluted with water, preferably with water for injection (WFI) i.e., pyrogen-free water. Alternatively, the extract can be dialyzed against the desired low conductivity buffer.

The flowthrough material is next adjusted to an appropriate pH and conductivity for the cation purification exchange step. The material may also be concentrated to reduce the flowthrough volume. One preferred buffer solution, or application buffer, is 50 mM phosphate buffer, pH 6.

In addition to adjusting the solution for the cation exchange step, the majority of low molecular weight contaminants are preferably removed at this stage by concentration, dialysis and/or diafiltration (ultrafiltration), using membranes with MW cutoffs about a 3,500 to 10,000 daltons. One preferred method of carrying out diafiltration of the material is given in Example 5. As seen from the HPLC profile in FIG. 2C, the filtration step has removed virtually all of the low molecular weight contaminants.

In the final purification step, the partially purified material (FIG. 2C) is applied to a cation exchange material, in the above application buffer. The cation exchange material is then washed extensively, until the elution profile reaches a baseline value, typically with about 15 to 20 column volumes of buffer. The extensive washing removes loosely bound material, including endotoxins and high molecular weight lipopolysaccharides (LPS), and is necessary for achieving high purity TCS.

TCS is then removed from the column in highly purified form by elution with a buffer whose salt concentration is just sufficient to release bound TCS from the cation exchange material. A preferred elution buffer, for use with SP (sulphoropyl) ZETAPREP ™ cation exchange material, is 50 mM phosphate buffer, pH 6.0 containing 60 mM NaCl (conductivity about 9.19 mS/cm), as described in Example 5. The eluted TCS protein is concentrated and dialyzed against a desired storage medium. As seen from the HPLC profile in FIG. 2D, the eluate protein is substantially free of contaminating proteins.

A variety of cation exchange materials have been tested for their ability to purify TCS from the partially purified extract, and the results are summarized in Example 5. Briefly, each of the five different materials tested resolved TCS from the extract, with highest resolution (TCS purity) being achieved by (a) SP ZETAPREP ™, applied in 50 mM phosphate, pH 6.0, and eluted with 50 mM phosphate, pH 6.0, containing 60 mM NaCl; (b) Pharmacia S-SEPHAROSE; applied in 20 mM phosphate, pH 6.0, and eluted with 50 mM phosphate, pH 6.0, containing 60 mM NaCl; and (c) PHOENIX SP13 ™, using the same application and elution buffers as in (b).

The TCS-containing eluent can be concentrated, ultrafiltered and sterile filtered to reduce the volume and to provide a TCS composition in a desired formulation buffer for use.

II. Purified TCS Composition

In another aspect, the present invention includes a substantially pure TCS composition (defined herein as having a purity of at least about 95%). Preferably, the composition has a purity of 98% or greater. The chemical purity of TCS protein produced as above was confirmed by HPLC, SDS gel electrophoresis, and isoelectric focusing methods. FIGS. 2A-2D are typical size-exclusion HPLC profiles of TCS-containing extract material at various stages of the purification method, showing the increased purity of the 11.3 min RT peak (BIOSIL TSK125) identified with TCS in the total clarified extract (2A), the flowthrough material from the anion exchange material (2B), the flowthrough material following diafiltration to remove low-molecular weight contaminants (2C), and the purified TCS (2D) obtained by the final ion-exchange step. As seen in FIG. 2D, there are no detectable contaminant peaks present in the HPLC profile. The limit of protein detection by this method indicates that the TCS protein preparation is at least about 98% pure.

A preparation of purified TCS purified as above was applied, in amounts ranging from 0.25 ug to 40 ug to a sodium doderyl sulfate (SDS) polyacrylamide slab gel. After fractionation by electrophoresis the gel was stained with Coomassie Blue stain.

Figure 3:
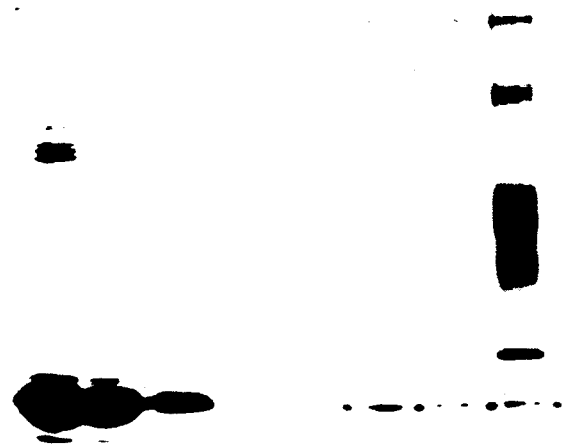

FIG. 3 shows the relative staining of the nine lanes with the different amounts of applied protein. Minor protein contaminant bands are seen in the gel lanes with 40 μg, 30 μg, and 20 μg protein, but not 10 μg or less. The limit of protein detection, as judged by the lowest amount of applied TCS which gave a visible band, is about 0.25 μg. It can be concluded from the gel staining patterns above that 10 μg of the purified TCS protein contains less than about 0.25 μg of contaminating protein. That is, the TCS is at least about 97.5% pure.

Figure 4:
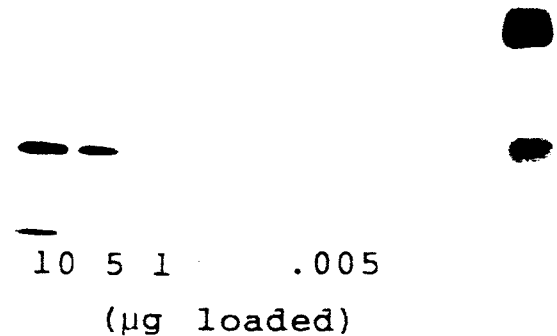

FIG. 4 shows the results of a similar gel-stain study in which the above purified TCS preparation was applied to an SDS gel slab at concentrations ranging from 0.005 μg to 10 μg. After electrophoresis, the slab was stained with silver. The limit of detection, as evidenced by the lowest amount of TCS which was detectable was 0.005 μg.

As seen from FIG. 4, no detectable contaminant bands were observed at 1 μg protein. Thus a 1 μg sample of purified TCS contains no more than about 0.005 μg contaminating protein. Judged by this gel-stain result, the TCS protein is at least about 99.5% pure.

Isoelectric focusing of the above purified TCS preparation and of a TCS preparation prepared by a prior art method (Yueng), and referred to below as "P. A.", was carried out in a PHAST system, supplied by Pharmacia, according to manufacturer's instructions in pH 3-9 gradient gels. The gels were fixed and silver stained.

The positions of the bands observed for the two TCS fractions are indicated in Table I below. The pH values shown in the table were calculated from the relationship pH =9.62−0.16×(distance from cathode in mm). This line equation was obtained from a standard curve (pH 3-10).

The major band in both TCS preparations is at the top of the gel, as expected, since the isoelectric point of TCS is about 9.6. In the purified TCS fraction, this band represents about 95% of the total protein. In the P. A. preparation, the upper band constitutes a significantly smaller percentage of the preparation. It is not known which, if any, of the contaminant bands in the two TCS preparations represent deamination and/or oxidation products of TCS. Clearly, however, the P. A. preparation contains many more contaminants than the TCS preparation of the present invention.

TABLE I

| Sample | Band Distance from cathode (mm) | Calculated pH |
|---|---|---|
| TCS- | 0 | ≧9 |
| (present invention) | 5 | 8.82 |
|  | 15 | 7.23 |
| P.A. | 0 | ≧9 |
|  | 5 | 8.82 |
|  | 6 | 8.66 |
|  | 15 | 7.23 |
|  | 16 | 7.07 |
|  | 22 | 6.10 |
|  | 23 | 5.94 |
|  | 29 | 4.98 |

In another of the invention, there is provided a purified TCS composition which is substantially free of hemagglutinins, e.g., lectins. At least three isolectins have been isolated from an acetone extract of *T. kirilowii* (Yeung) and studies performed in support of the present invention have identified at least one protein contaminant (a 10.3 min RT peak seen on BIOSIL TSK250Q) with hemagglutination activity. As noted above, hemagglutinin contaminants present in the original plant extract are substantially completely removed in the anion exchange purification step, when carried at a low conductivity, and preferably at a relatively low flow rate.

Additional studies carried out in support of the present invention indicate that the purified TCS preparation herein shows no detectable hemagglutination activity, even at a TCS concentration of about 20 mg/mL.

The TCS Composition of the invention also contains a substantially reduced amount of endotoxin. As seen from a comparison of the size-exclusion HPLC profiles in FIG. 2B and 2C, virtually all of the high molecular weight contaminants (which include endotoxins) are removed by the cation exchange step. The removal of endotoxins was confirmed by limulus amoebocyte lysate (LAL) assay (U.S. Pharmacopeia).

III. Utility

A. Abortifacient Activity

As noted above, TCS, or impure plant extracts containing TCS, have been used as an abortifacient agent for inducing abortion in humans, particularly during midtrimester (14 to 26 weeks). The protein can be administered by intramuscular, intravenous, or intraamniotic routes, typically at a single dose of between about 5-12 mg.

B. Treating HIV Infection in Humans

The discovery that viral expression and cell proliferation of HIV-infected T cells and monocyte/macrophages can be selectively inhibited by TCS has been described in co-owned U.S. Pat. No. 4,795,739 for "Method of Inhibiting HIV". An important aspect of the discovery was the finding that viral inhibition in HIV-infected cells could be achieved at concentrations of TCS which are substantially non-toxic to uninfected cells. This selective effect was evidenced by marked decreases in viral antigen associated with HIV-infected cells, and in measurable reverse transcriptase activity, several days after exposure to TCS, without a corresponding decrease in expression of non-viral proteins. Another aspect of the selective inhibitory effect of TCS is a substantial loss of cell viability in HIV-infected cells, at TCS concentrations which did not significantly reduce the viability of non-infected cells. Typically, these selective inhibition effects were seen at TCS concentrations between about 0.01-3.0 ug/ml.

The viral inhibition effects of TCS on HIV-infected T cells and monocyte/macrophages can be exploited in the treatment of HIV infection in humans. The ability of TCS to inhibit viral replication in infected cells, as evidenced by the sharp decline in reverse transcriptase activity associated with the cells, would reduce the level of infection, with the possibility of eliminating the virus "reservoir" which may be provided by the monocyte/macrophages and other peripheral blood cells (Grove; Gartner, 1986a, 1986b; Koenig; Ho; Chayt; Armstrong; Steicher).

Secondly, recent evidence suggests that the fusion of CD4+T cells with infected T cells or monocyte/macrophages requires the presence of the HIV gp120 antigen, on the surface of the infected cells (Lifson, 1986a, 1986b, 1986c). One striking effect of TCS is the ability to inhibit and substantially eliminate expression of viral antigens, such as gp120, in infected cells.

TCS may also inhibit or prevent other events related to the loss of immunological competence in HIV infected individuals, through general suppression of virus levels and inhibition of viral protein synthesis in infected cells.

At the same time, and according to another important aspect of the TCS treatment, the levels of protein which are effective in preventing viral antigen production are only slightly cytotoxic to non-infected blood cells. Effective levels of TCS were in the range 0.2 to 3 μg/mL cell suspension. Assuming a uniform distribution of the drug throughout the bloodstream of a treated individual (7 liter volume), this concentration of drug is achieved with a parenteral injection of between about 1.5 to 20 mg. This is within the same range of TCS used for inducing abortion in humans (about 5–12.5 mg), a general level which can be administered without serious side effects (Kuo-Fen), as discussed above.

From the foregoing, it can be appreciated how various objects and features of the invention are met. The TCS purification method of the invention yields a highly purified TCS protein suitable for intravenous therapeutic administration. In particular, the preparation is substantially free of hemagglutinins and endotoxins.

The method is readily adapted to large scale protein production, since (a) organic-solvent extraction steps with volatile organic solvents are avoided, and (b) the anion and cation exchange steps can be carried out in a batch-wise fashion, without the need for salt-gradient or molecular sieve chromatography separation.

The following examples illustrate preferred methods according to the invention, but are in no way intended to limit the scope of the invention.

EXPERIMENTAL

Materials

*T. kirilowii* root tubers were obtained from the People's Republic of China.

HPLC chromatography was carried out with either a BIOSIL TSK125 or BIOSIL TSK250 column obtained from BioRad (Richmond, Calif.), using isocratic elution with a 1.0 mL/min flow rate and mobile phase of 0.1 M $Na_2SO_4$, 0.02 M $NaH_2PO_4/Na_2HPO_4$, pH 6.8±0.2.

QAE ZETAPREP TM anion exchange cartridges and SP ZETAPREP TM cation exchange cartridges were supplied by AMF Cuno Corp. (Meridan, Conn.); PHOENIX SP13 cation exchange resin was obtained from Astec (Whispany, N.J.); Pharmacia S-SEPHAROSE from Pharmacia (San Diego, Calif.); IBF SEPHERODEX M and IBF SP TTRISACRYL M, from IBF Biotechnics (Savage, Md.); PELLICON ultrafiltration membranes (10,000 MW cutoff), from Millipore Corp. (Bedford, Mass.); 0.45 and 0.22 micron pleated capsule filters from Gelman Corp. (Ann Arbor, Mich.). A YM5 (5,000 MW cutoff) ultrafiltration membrane was obtained from Amicon/W. R. Grace (Danvers, Mass.).

EXAMPLE 1

Preparation of Trichosanthin

This example illustrates a preferred method of producing purified TCS according to the invention. Novel features of the purification method are described in greater detail in the following examples.

Except where noted, steps of the procedure described below were carried out at room temperature.

Frozen root tubers of *T. kirilowii* were thawed at room temperature by placing them in water or saline for two to three hours. The tubers were peeled, sliced into small pieces and homogenized in a juicer in normal saline (0.9% NaCl) to form a homogenate. The homogenate was passed through gauze to remove pulp, adjusted to pH 8.0 with NaOH and stirred either for one hour at room temperature or overnight at 2°–8° C. to form an extraction.

The extraction was clarified by centrifugation at 7,000×g for 15 min at 4° C. and the pellet was discarded. FIG. 2A shows a typical size-exclusion HPLC profile (BIOSIL TSK125) of the clarified extraction. The 11.3 min. RT peak (BIOSIL TSK125) in this chromatogram contains the TCS.

The supernatant was purified by elution through a QAE ZETAPREP TM anion exchange cartridge using 20 mM sodium phosphate buffer, pH 8.0 and the flowthrough was collected. A typical size-exclusion HPLC profile of the flowthrough is shown in FIG. 2B. The solution was substantially free of a 9.7 min. RT peak (BIOSIL TSK250) associated with hemagglutination activity.

The flowthrough was clarified by filtration over a 0.45 μm filter pleated capsule filter. The filtered flowthrough was concentrated by ultrafiltration using a PELLICON cartridge membrane with a 10,000 MW cutoff. The concentrated flowthrough was diafiltered using the PELLICON cartridge against 50 mM sodium phosphate, pH 6.0 to adjust the conductivity. The permeate was discarded and the retentate was clarified by filtration through a 0.45 μm filter pleated capsule filter. The retentate was substantially free from small molecular weight contaminants, as shown from the absence of peaks in the range above about 11.3 min. RT (BIOSIL TSK125) in the size-exclusion HPLC shown in FIG. 2C.

The following steps were carried out in a controlled environment to minimize the amount of biological contaminants added to the preparation during processing. All of the buffers were filtered using a 0.22 μm pleated capsule filter prior to use.

The filtered retentate from the previous step was loaded onto an SP ZETAPREP TM cation exchange cartridge equilibrated with 50 mM phosphate buffer, pH 6.0. After loading, the cartridge was washed extensively with about 15 to about 20 times the column volume of buffer to ensure removal of weakly bound contaminants (associated with endotoxin activity). TCS protein was eluted in 50 mM sodium phosphate buffer pH 6.0, 60 mM NaCl and collected in fractions and stored overnight at 4° C. The TCS-containing fractions were approximately 98% pure, as determined by size-exclusion HPLC, and SDS gel electrophoresis. The eluent is substantially free from endotoxin, as determined by Limulus Amoebocyte Lysate (LAL) analysis.

The TCS-containing fractions were pooled and concentrated using a PELLICON cartridge membrane with a 10,000 MW cutoff. The permeate was discarded. The retentate was diafiltered against a suitable phosphate buffer and filter sterilized by passage through a 0.22- μm membrane.

EXAMPLE 2

Anion Exchange Procedures

Optimal Ionic Strength

All experiments were run at a flow rate of 2mL/min on a QAE ZETAPREP TM 60 disk. Prior to sample loading, the QAE ZETAPREP TM cartridge was equilibrated with phosphate buffer having the same conductivity as the sample. Following the procedure, the QAE ZETAPREP TM was regenerated with 0.1 M acetic acid followed by 1.0M NaCl. All experiments used the same clarified batch extracted in saline. The protein concentration of the clarified extract was 16.9 mg/mL as determined by the Lowry method (Lowry).

Samples (75 or 30 mL) of the extract were diluted with pyrogen-free water to yield a solution of 2.9 mS/cm conductivity at pH 8.0. When the clarified extract was diluted to about 2.9 mS/cm conductivity, a significant amount of precipitate was observed. As determined by HPLC using a BIOSIL TSK250 column (BioRad, Richmond, Calif.), the precipitate was the highest molecular weight contaminant (HPLC peak about 6.8 min. RT).

The contaminant having a 6.8 min. RT peak did not bind in any significant amount to the QAE ZETAPREP TM when the application buffer was greater than about 40 mM in phosphate, pH 8.0. However, the 6.8 RT peak was decreased significantly in the diluted, 20 mM phosphate buffer, pH 8.0, due to precipitation and subsequent entrapment in the anion exchange material. A 9.0 min. RT peak contaminant bound almost completely to the QAE ZETAPREP TM when a 30 mL (507 mg protein) sample was loaded. However, when using a larger sample, the 9.0 min. RT peak appeared in the flowthrough after approximately 500 mg of protein had been loaded. Some of this protein peak was also seen in later fractions when using 40 mM sodium phosphate, pH 8.0. A 10.3 min. RT peak contaminant bound better to the cartridge when the buffer conductivity was below that of 50 mM sodium phosphate. No 10.3 min. RT peak was observed in the flowthrough at 20 mM phosphate, pH 8.0. The low molecular weight proteins were seen in almost all of the flowthrough fractions. The presence of low MW proteins was not of major concern since the subsequent diafiltration step efficiently removed those proteins. These results can be appreciated from the HPLC profile shown in FIG. 2B which shows the substantial removal of peaks eluting ahead of the 11.3 min RT TCS peak on BIOSIL TSK125 HPLC.

The results of this study demonstrated that the use of solutions having low ionic strength (low conductivity) improve the effectiveness of the QAE ZETAPREP anion exchange step. By diluting the sample to a conductivity approximately of 20mM sodium phosphate, pH 8.0, (about 3.08 mS/cm) the 6.9 RT peak contaminant was removed by precipitation and the 9.0 and 10.3 RT peaks bound more efficiently to the anion exchange material disk.

EXAMPLE 3

Removal of Hemagglutinins

As noted in Example 2, a low ionic strength medium is required for removal of a 10.3 min RT peak contaminant by anion exchange. The study described below shows that the anion exchange material binding conditions which are effective in removing the 10.3 min RT peak also effectively remove hemagglutinins from the partially purified flowthrough material.

Clarified extracts prepared as in Example 1 were equilibrated to 100 mM or 20 mM sodium phosphate buffer, pH 6.8. The extract material was added to QAE-anion exchange material equilibrated with the same buffer, i.e., 100 mM or 20 mM sodium phosphate. In the case of protein binding at 100 mM sodium phosphate, flowthrough fractions corresponding approximately to the 6.8 (fraction #2), 10.35 (fraction #5) and 17.46 (fraction #9) min. RT peaks seen in BIOSIL TSK250 HPLC profiles. For the case of binding at 20 mM sodium phosphate, flowthrough fractions corresponding approximately to the 6.8 (fraction #2), 9.040 (fraction #4) and 10.03 (fraction #5) min. RT peaks were collected.

The collected fractions were assayed for hemagglutination activity by a standard hemagglutination test. Briefly, a 50 μl aliquot of each fraction, diluted in 0.9% NaCl as indicated in Table II below, was added to about ≈200 μl of a 5% human O-negative erythrocyte suspension centrifuged for 15 sec (SEROFUGE), and hemagglutination was recorded in a serological scale of 0 to 4+. Ten minutes after incubation at 25°±3° C. the samples are read again for hemagglutination. The blood samples were examined visually for the presence of detectable agglutination. The tests results are expressed as number of positive agglutinations/total number of assays. For example, a result of ⅓ indicates one positive agglutination in 3 tests.

Also tested were diluted aliquots of the unpurified extract and a TCS preparation purified according to published methods.

TABLE II

| Sample | Hemaglutination dilution: | | |
|---|---|---|---|
| | 1:1 | 1:2 | 1:4 |
| Extract | 4/4 | 4/4 | 4/4 |
| F2: 100 mM sodium phosphate | 0/4 | 0/4 | 0/4 |
| F5: 100 mM sodium phosphate | 4/4 | 4/4 | 4/4 |
| F9: 100 mM sodium phosphate | 4/4 | 4/4 | 3/3 |
| F2: 20 mM sodium phosphate | 0/4 | 0/4 | 0/4 |
| F4: 20 mM sodium phosphate | 0/4 | 0/4 | 0/4 |
| F5: 20 mM sodium phosphate | 0/4 | 0/4 | 0/4 |
| P.A. | 3/3 | 2/3 | 1/3 |

The data show that fractions 5 and 9 from the 100 mM sodium phosphate anion exchange material wash have high hemagglutination activity. By contrast, none of the fractions collected in the 20 mM sodium phosphate wash show detectable hemagglutination activity. It is also noteworthy that the TCS protein (P. A.) purified according to a previously published method (Yeung) shows relatively high hemagglutination activity.

EXAMPLE 4

Concentration and Ultrafiltration

Major low-molecular weight contaminants are removed, in accordance with the purification method, by concentration and/or dialysis (or diafiltration) using membranes with 3,500–10,000 dalton MW cut-offs. FIG. 2B shows the size-exclusion HPLC profile of plant extract prior to concentration with a PTGC cassette 10,000 MW cut-off ultrafiltration membrane. When the retentate of the concentration procedure was run on size-exclusion HPLC, the profile seen in FIG. 2C was obtained. The figure shows that low molecular weight proteins were largely removed, but that high MW proteins, including the TCS protein, were not.

Diafiltration with a 10,000 MW cut off membrane produced a similar reduction in the peaks of lower molecular weight proteins. When the two procedures are combined, the protein peaks eluting after the TCS peak (11.3 min. RT) in the size-exclusion HPLC (BIOSIL TSK125) profiles were virtually eliminated.

EXAMPLE 5

Cation Exchange Procedures

Cation exchange purification of the above partially purified extract was carried out in the following manner. A protein preparation produced from a plant extract, after anion exchange binding (Example 2) was equilibrated with 50 mM sodium phosphate, pH 6.0 (conductivity 3.6 mS/cm) by diafiltration, using a 10,000 MW cut-off membrane as described in Example 4. Following diafiltration, the material was loaded onto the SP ZETAPREP TM column, and the column was washed with 50 mM sodium phosphate, pH 6.0 washed extensively (15-20 volumes) with 50 mM sodium phosphate buffer, pH 6.0, until the chromatogram returned to base line. The TCS was eluted with 50 mM sodium phosphate, 60 mM NaCl (conductivity 9.19 mS/cm). The TCS protein which eluted from the column was examined by size-exclusion HPLC, with the results shown in FIG. 2D. Following elution of TCS, the column was stripped with 50 mM sodium phosphate, 1.0 M NaCl, yielding high molecular weight contaminants.

Several cation exchange materials were investigated for their ability to bind TCS under conditions which allow elution of TCS in pure form. Summarizing the results obtained:

(a) Phoenix SP13 was tested at initial 20 mM or 50 mM sodium phosphate buffer concentrations. The resin showed poor binding of material at 50 mM sodium phosphate buffer, pH 6.0, but gave good separation of TCS at an initial binding at 20 mM buffer, when followed by extensive washing with the same buffer and TCS elution with 50 mM sodium phosphate, 60 mM NaCl, pH 6.0.

(b) Pharmacia S-SEPHAROSE was also tested at initial 20 mM and 50 mM sodium phosphate buffer concentrations. The resin showed strong binding of TCS at 20 mM phosphate buffer, pH 6.0, and release of a substantially pure protein with elution at 50 mM phosphate buffer, 60 mM NaCl, pH 6.0.

(c) IBF SP SEPHERODEX M required higher salt concentration for TCS release.

(d) IBF SP TRISACRYL M was tested at initial 50 mM phosphate, pH 6.0, buffer concentration. The resin showed strong binding of TCS at this concentration and eluted from the resin at 50 mM buffer, 60 mM NaCl, pH 6.0

In summary, all of the cation exchange resins were acceptable substitutes for the SP ZETAPREP cartridge. PHOENIX SP13 and Pharmacia S-SEPHAROSE at 20 mM sodium phosphate, pH 6.0, were most comparable in performance to SP ZETAPREP.

While the invention has been described with reference to specific methods and embodiments, it will be appreciated that various modifications and changes may be made without departing from the invention.

It is claimed:

1. A method of producing trichosanthin, comprising:
    (a) preparing a single-aqueous phase clarified plant extract from the roots of Trichosanthes kirilowii;
    (b) contacting the extract with an anion exchange material, wherein said anion exchange material has a quaternary ethylamino ethyl functional group, and the extract contacted with the anion exchange material has a conductivity of less than about 3-3.5 mS/cm and a pH of between about 7-9, to produce a substantially hemagglutinin free eluent;
    (c) contacting the eluent of step (b) with a cation exchange material, wherein the cation exchange material has a sulphopropyl functional group, and said contacting includes binding extract material with the cation exchange material at a conductivity of about 3-4 mS/cm, washing the cation exchange material extensively to remove weakly bound contaminants; and,
    (d) releasing purified trichosanthin from said cation exchange material by washing with a solution of a conductivity of about 9.0 mS/cm.

2. The method of claim 1, which further includes removing small molecular weight contaminants by membrane ultrafiltration or dialysis.

3. The method of claim 1, wherein the trichosanthin is substantially free of hemagglutinins as evidenced by use of a standard O-negative erythrocyte hemagglutination test.

4. The method of claim 1, wherein the protein purity of trichosanthin is greater than about 98%.

5. A method of producing trichosanthin, comprising:
    (a) preparing a single-aqueous phase clarified plant extract from the roots of Trichosanthes kirilowii, said extract having a conductivity of less than about 3.5 mS/cm;
    (b) contacting the extract with an anion exchange material, having quaternary ethylamino ethyl functional groups, to produce a substantially hemagglutinin free eluent;
    (c) treating said eluent by membrane ultrafiltration or dialysis to produce a retentate that is substantially free of contaminants having a molecular weight of less than about 10,000 daltons;
    (d) contacting said retentate with a cation exchange material, having a sulphopropyl functional group, at a conductivity between about 3-4 mS/cm;
    (e) washing the cation exchange material extensively to remove weakly bound contaminants;
    (f) treating the cation exchange material with a solution having a conductivity of about 9.0 mS/cm sufficient to release trichosanthin from the cation exchange material; and
    (g) collecting the released trichosanthin having a purity of greater than about 95% and which is substantially free of hemagglutinins as evidenced by use of a standard O-negative erythrocyte hemagglutination test.

* * * * *